United States Patent [19]
Mohr et al.

[11] Patent Number: 6,040,259
[45] Date of Patent: Mar. 21, 2000

[54] METAL-CONTAINING ZEOLITE CATALYST, PREPARATION THEREOF AND USE FOR HYDROCARBON CONVERSION

[75] Inventors: Gary David Mohr, League City, Tex.; Johannes Petrus Verduijn, Rotterdam, Netherlands

[73] Assignee: Exxon Chemical Patents Inc., Houston, Tex.

[21] Appl. No.: 08/865,727

[22] Filed: May 29, 1997

Related U.S. Application Data

[60] Provisional application No. 60/018,583, May 29, 1996.

[51] Int. Cl.<sup>7</sup> ..................................... B01J 29/06
[52] U.S. Cl. ............................ 502/67; 502/64; 502/66; 502/69; 502/74; 502/77
[58] Field of Search ................... 502/64, 66, 67, 502/69, 74, 77

[56] References Cited

U.S. PATENT DOCUMENTS 5,460,796  10/1995  Verduijn .................................. 423/700
5,486,348   1/1996  Verduijn et al. ......................... 423/700

FOREIGN PATENT DOCUMENTS 0284206   9/1988  European Pat. Off. .
1511892   5/1978  United Kingdom .
WO9616004  5/1996  WIPO .

*Primary Examiner*—Thomas Dunn
*Attorney, Agent, or Firm*—Edward F. Sherer

[57] ABSTRACT

There is provided a zeolite bound zeolite catalyst which does not contain significant amounts of non-zeolitic binder and a process for converting hydrocarbons utilizing the zeolite bound zeolite catalyst. The catalyst comprises first zeolite, crystals, a binder comprising second zeolite crystals and a hydrogenation/dehydrogenation metal. The zeolite bound zeolite catalyst is prepared by converting the silica binder of a silica bound aggregate containing the first crystals of said first zeolite and at least a portion of the hydrogenation/dehydrogenation metal to said second zeolite. The zeolite bound zeolite catalyst has excellent performance when used in hydrocarbon conversion processes such as naphtha reforming and xylenes isomerization/ethylbenzene conversion.

41 Claims, 2 Drawing Sheets

METAL-CONTAINING ZEOLITE CATALYST, PREPARATION THEREOF AND USE FOR HYDROCARBON CONVERSION

This application claims benefit of provisional application 60/018,583, filed May 29, 1996.

FIELD OF THE INVENTION

This invention relates to a method of preparing zeolite bound zeolite catalysts having enhanced hydrogenation/dehydrogenation metal dispersion, the catalyst itself, and the use of the catalyst in hydrocarbon conversion processes.

BACKGROUND OF THE INVENTION

Crystalline microporous molecular sieves, both natural and synthetic, have been demonstrated to have catalytic properties for various types of hydrocarbon conversion processes. In addition, the crystalline microporous molecular sieves have been used as adsorbents and catalyst carriers for various types of hydrocarbon conversion processes, and other applications. These molecular sieves are ordered, porous, crystalline materials having a definite crystalline structure as determined by x-ray diffraction, within which there are a large number of smaller cavities which may be interconnected by a number of still smaller channels or pores. The dimensions of these channels or pores are such as to allow for adsorption of molecules with certain dimensions while rejecting those of large dimensions. The interstitial spaces or channels formed by the crystalline network enable molecular sieves such as crystalline silicates, crystalline aluminosilicates crystalline silicoalumino phosphates, and crystalline aluminophosphates, to be used as molecular sieves in separation processes and catalysts and catalyst supports in a wide variety of hydrocarbon conversion processes.

Zeolites are comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, titanium oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as silicoaluminophosphates (SAPO) and aluminophosphates (ALPO). The term "aluminosilicate zeolite", as used herein, shall mean zeolite materials consisting essentially of silicon and aluminum atoms in the crystalline lattice structure thereof.

Zeolites such as ZSM-5, that have been combined with a Group VIII metal have been used in the past as catalysts for hydrocarbon conversion. For example, U.S. Pat. No. 3,856,872 discloses a zeolite preferably containing a binder such as aluminia that has been loaded with platinum by impregnation or ion exchange. A problem associated with zeolite catalysts that have been loaded with metals by impregnation or ion exchange is that the metal may not be well dispersed. If the metal is not well dispersed, selectivity, activity and/or activity maintenance of the zeolite catalyst can be adversely effected.

U.S. Pat. No. 4,312,790 discloses another method of loading platinum on an alumina bound zeolite. The method involves adding the noble metal to the zeolite after crystallization of the zeolite, but before calcination. Catalysts prepared by this method have not been commercially useful because, as reported in U.S. Pat. No. 4,683,214, the use of the method has resulted in catalysts with poor platinum dispersion and large platinum crystallites.

Synthetic zeolites are normally prepared by the crystallization of zeolites from a supersaturated synthesis mixture. The resulting crystalline product is then dried and calcined to produce a zeolite powder. Although the zeolite powder has good adsorptive properties, its practical applications are severely limited because it is difficult to operate fixed beds with zeolite powder. Therefore, prior to using the powder in commercial processes, the zeolite crystals are usually bound.

The zeolite powder is typically bound by forming a zeolite aggregate such as a pill, sphere, or extrudate. The extrudate is usually formed by extruding the zeolite in the presence of a non-zeolitic binder and drying and calcining the resulting extrudate. The binder materials used are resistant to the temperatures and other conditions, e.g., mechanical attrition, which occur in various hydrocarbon conversion processes. Examples of binder materials include amorphous materials such alumina, silica, titania, and various types of clays. It is generally necessary that the zeolite be resistant to mechanical attrition, that is, the formation of fines which are small particles, e.g., particles having a size of less than 20 microns.

Although such bound zeolite aggregates have much better mechanical strength than the zeolite powder, when such a bound zeolite is used in a catalytic conversion process, the performance of the zeolite catalyst, e.g., activity, selectivity, activity maintenance, or combinations thereof, can be reduced because of the binder. For instance, since the binder is typically present in an amount of up to about 50 wt. % of zeolite, the binder dilutes the adsorption properties of the zeolite aggregate. In addition, since the bound zeolite is prepared by extruding or otherwise forming the zeolite with the binder and subsequently drying and calcining the extrudate, the amorphous binder can penetrate the pores of the zeolite or otherwise block access to the pores of the zeolite, or slow the rate of mass transfer to the pores of the zeolite which can reduce the effectiveness of the zeolite when used in xylene isomerization. Furthermore, when the bound zeolite is used in catalytic conversion processes, the binder may affect the chemical reactions that are taking place within the zeolite and also may itself catalyze undesirable reactions which can result in the formation of undesirable products.

In certain hydrocarbon conversion processes involving dehydrogenation and dehydrocyclization reactions, it is desirable that the zeolite catalyst used in the process be effective for metal-catalyzed reactions, e.g., conversion of paraffins to aromatic products. In order for the catalyst to be effective for metal catalyzed reactions, a catalytically active metal is usually included in the catalyst. The catalytically active metal should be uniformly dispersed. If the metal is not uniformly dispersed, the activity, selectivity, and/or activity maintenance of the catalyst can be adversely effected.

Accordingly, it would be desirable to produce zeolite catalysts which have uniformly dispersed hydrogenation/dehydrogenation metals and do not contain substantial amounts of non-zeolitic binder.

SUMMARY OF THE INVENTION

In accordance with the present invention, there is provided a zeolite bound zeolite catalyst and a process for preparing the zeolite bound zeolite catalyst. The catalyst comprises first crystals of a first zeolite, a binder comprising second crystals of a second zeolite, and a hydrogenation/dehydrogenation metal. The process is carried out by converting the silica binder of a silica bound extrudate which also contains the first crystals of the first zeolite and the hydrogenation/dehydrogenation metal, into the second zeolite.

In another embodiment, the present invention provides a process for the conversion of hydrocarbon feeds using the zeolite bound zeolite catalyst in a process or combination of processes which employs a hydrogenation/dehydrogenation metal such as a Group VIII metal. Examples of such processes include hydrogenation, dehydrogenation, dehydrocyclization, isomerization, cracking, dewaxing, reforming, conversion of alkylaromatics, oxidation, synthesis gas conversion, hydroformylation, dimerization, polymerization, and alcohol conversion.

When used in processes such as naphtha reforming and xylene isomerization, the zeolite bound zeolite catalyst exhibits high hydrogenation/dehydrogenation activity which results in the production of desired products while at the same time exhibits reduced cracking activity which is undesirable in these processes.

DETAILED DESCRIPTION OF THE INVENTION

Figure 1:
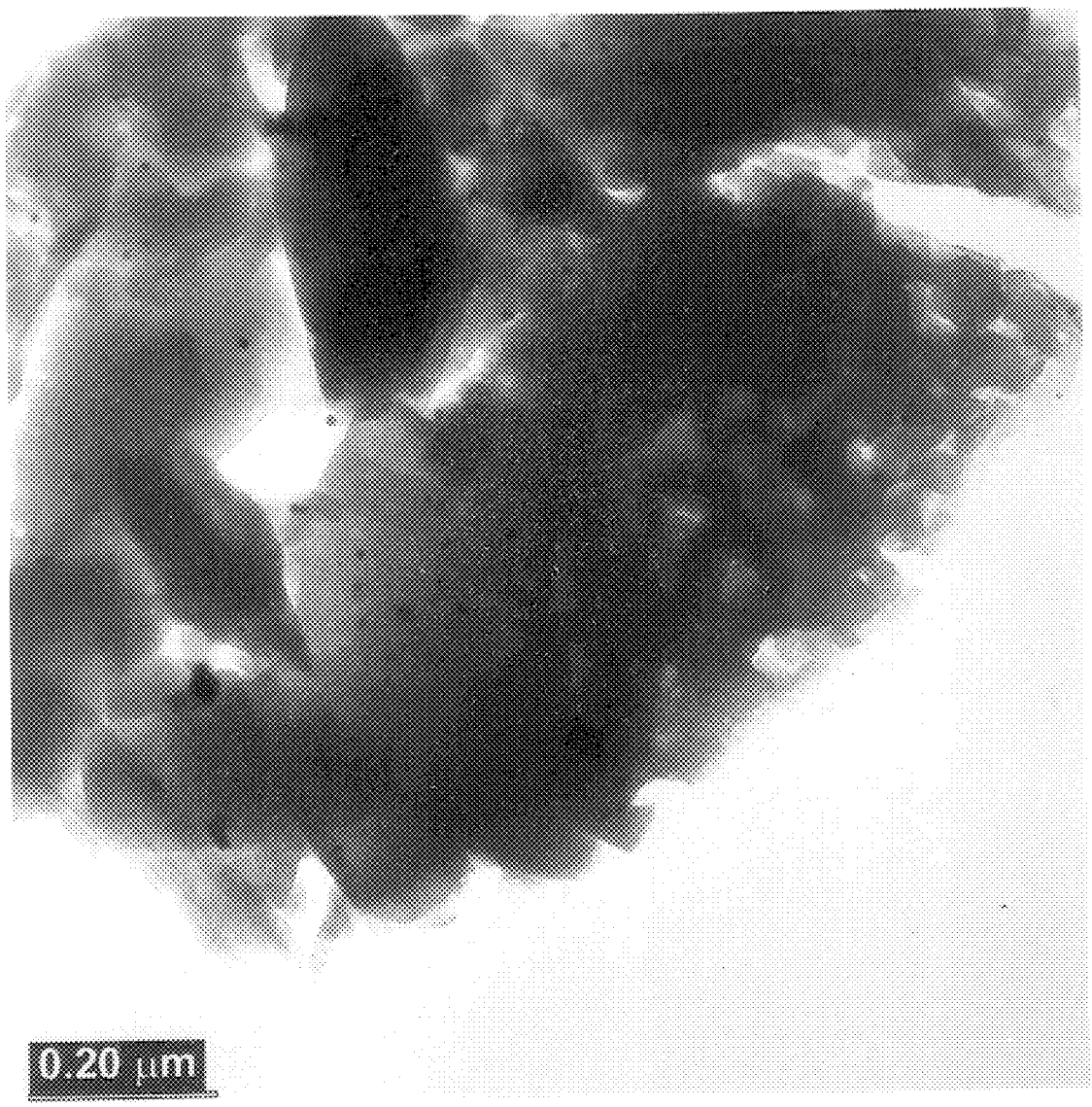
FIG. 1 represents an electron micrograph of the catalyst prepared in Example 1.I.

The zeolite bound zeolite catalyst comprises first crystals of a first zeolite, a binder comprising second crystals of a second zeolite, and a hydrogenation/dehydrogenation metal. In preparing the zeolite bound zeolite catalyst, the hydrogenation/dehydrogenation metal is present in the silica bound extrudate which contains the first zeolite prior to converting the silica binder to the second zeolite. The resulting zeolite bound zeolite catalyst has enhanced hydrogenation/dehydrogenation metal dispersion. In addition, the use of the second crystals of the second zeolite as a binder results in a catalyst which provides a means for controlling undesirable reactions taking place on or near the external surface of the first zeolite crystals and can have improved mass transfer of hydrocarbon molecules to and from the pores of the first zeolite.

Unlike typical zeolite catalysts used in hydrocarbon conversion processes which are normally bound with silica or alumina or other commonly used amorphous binders to enhance the mechanical strength of the zeolite, the zeolite catalyst of the present invention generally does not contain significant amounts of non-zeolitic binders.

Preferably, the zeolite bound zeolite catalyst contains less than 10 percent by weight, based on the weight of the first and second zeolite, of non-zeolitic binder, more preferably contains less than 5 percent by weight, and, most preferably, the catalyst is substantially free of non-zealitic binder. Preferably, the second zeolite crystals bind the first zeolite crystals by adhering to the surface of the first zeolite crystals thereby forming a matrix or bridge structure which also holds the first crystals particles together. More preferably, the second zeolite particles bind the first zeolite by intergrowing so as to form a coating or partial coating on the larger first zeolite crystals and, most preferably, the second zeolite crystals bind the first zeolite crystals by intergrowing to form an attrition resistant over-growth over the first zeolite crystals.

Although the invention is not intended to be limited to any theory of operation, it is believed that in addition to enhanced metal dispersion, another advantage of the zeolite bound zeolite catalyst of the present invention is obtained by the second zeolite crystals controlling the accessibility of the acid sites on the external surfaces of the first zeolite to reactants. Since the acid sites existing on the external surface of a zeolite catalyst are not shape selective, these acid sites can adversely affect reactants entering the pores of the zeolite and products exiting the pores of the zeolite. In line with this belief, since the acidity and structure type of the second zeolite can be carefully selected, the second zeolite does not significantly adversely affect the reactants exiting the pores of the first zeolite which can occur with conventionally bound zeolite catalysts and may beneficially affect the reactants exiting the pores of the first zeolite. Still further, since the second zeolite is not amorphous but, instead, is a molecular sieve, hydrocarbons may have increased access to the pores of the first zeolite during hydrocarbon conversion processes. Regardless of the theories proposed, the zeolite bound zeolite catalyst, when used in catalytic processes, has one or more of the improved properties which are disclosed herein.

The terms "acidity", "lower acidity" and "higher acidity" as applied to zeolite are known to persons skilled in the art. The acidic properties of zeolite are well known. However, with respect to the present invention, a distinction must be made between acid strength and acid site density. Acid sites of a zeolite can be a Bronsted acid or a Lewis acid. The density of the acid sites and the number of acid sites are important in determining the acidity of the zeolite. Factors directly influencing the acid strength are (i) the chemical composition of the zeolite framework, i.e., relative concentration and type of tetrahedral atoms, (ii) the concentration of the extra-framework cations and the resulting extra-framework species, (iii) the local structure of the zeolite, e.g., the pore size and the location, within the crystal or at/near the surface of the zeolite, and (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia absorption.

First and second zeolites suitable for use in the zeolite bound zeolite catalyst of the present invention include large pore size zeolites, intermediate pore size zeolites, and small pore size zeolites. These zeolites are described in "Atlas of Zeolite Structure Types", eds. W. H. Meier and D. H. Olson, Butterworth-Heineman, Third Edition, 1992, which is hereby incorporated by reference. A large pore zeolite generally has a pore size greater than about 7 Å and includes for example LTL, VFI, MAZ, MEI, FAU, EMT, OFF, BEA, and MOR structure type zeolites (IUPAC Commission of Zeolite Nomenclature). Examples of large pore zeolites, include, for example, mazzite, mordenite, offretite, zeolite L, VPI-5, zeolite Y, zeolite X, omega, Beta, ZSM-3, ZSM-4, ZSM-18, and ZSM-20. An intermediate pore size zeolite generally has a pore size from about 5 Å, to about 7 Å and includes for example, MFI, MFS, MEL, MTW, EUO, MTT, HEU, FER, and TON structure type zeolites (IUPAC Commission of Zeolite Nomenclature). Examples of intermediate pore size zeolites, include ZSM-5, ZSM-12, ZSM-22, ZSM-23, ZSM-34, ZSM-35, ZSM-38, ZSM-48, ZSM-50, silicalite, and silicalite 2. A small pore size zeolite generally has a pore size from about 3 Å to about 5.0 Å and includes for example, CHA, ERI, KFI, LEV, and LTA structure type zeolites (IUPAC Commission of Zeolite Nomenclature). Examples of small pore zeolites include ZK-4, SAPO-24, SAPO-35, ZK-14, SAPO-42, ZK-21, ZK-22, ZK-5, ZK-20, zeolite A, erionite, chabazite, zeolite T, gemlinite, ALPO-17, and clinoptilolite.

Generally, the first and second zeolites of the zeolite bound zeolite catalyst comprise compositions having the following molar relationship:

$$X_2O_3:(n)YO_2,$$

wherein X is a trivalent element, such as titanium, boron, aluminum, iron, and/or gallium, Y is a tetravalent element such as silicon, tin, and/or germanium, and n has a value of at least 1, said value being dependent upon the particular type of zeolite and the trivalent element present in the zeolite.

When either zeolite has an intermediate pore size, the zeolite usually comprises a composition having the following molar relationship:

$$X_2O_3:(n)YO_2,$$

wherein X is a trivalent element, such as aluminum, boron, titanium, and/or gallium, Y is a tetravalent element such as silicon, tin, and/or germanium; and n has a value greater than 10, said value being dependent upon the particular type of zeolite and the trivalent element present in the zeolite. When the first or second zeolite has a MFI structure, n is preferably greater than 10.

As known to persons skilled in the art, the acidity of a zeolite can be reduced using many techniques such as by dealumination and steaming. In addition, the acidity of a zeolite is dependent upon the form of the zeolite with the hydrogen form having the highest acidity and other forms of the zeolite such as the sodium form having less acidity than the acid form. Accordingly, the mole ratios of silica to alumina and silica to gallia disclosed herein shall include not only zeolites having the disclosed mole ratios, but shall also include zeolites not having the disclosed mole ratios but having equivalent catalytic activity.

When the first zeolite is a gallium silicate intermediate pore size zeolite, the zeolite usually comprises a composition having the following molar relationship:

$$Ga_2O_3:ySiO_2$$

wherein y is between about 10 and about 1000. The zeolite framework may contain only gallium and silicon atoms or may also contain a combination of gallium, aluminum, and silicon. When the first zeolite is a MFI structure type gallium silicate zeolite, the second zeolite will preferably be an intermediate pore size zeolite having a silica to gallia mole ratio greater than 100. The second zeolite can also have higher silica to gallia mole ratios, e.g., greater than 200, 500, 1000, etc.

When the first zeolite in the zeolite bound zeolite catalyst is an aluminosilicate zeolite, the silica to alumina mole ratio will usually depend upon the structure type of the first zeolite and the particular hydrocarbon process in which the catalyst is utilized and is therefore not limited to any particular ratio. Generally, however, and depending on the structure type of the zeolite, the first zeolite will have a silica to alumina mole ratio of at least 2:1 and in some instances from 4:1 to about 7:1. For a number of zeolites, the silica to alumina mole ratio will be in the range of from about 10:1 to about 1,000:1. In applications such as when the catalyst is utilized in acid catalyzed reactions, e.g., the isomerization of a feedstream containing xylenes and ethylbenzene, the first zeolite will be acidic and will preferably, especially when an intermediate pore size zeolite, have higher silica to alumina mole ratios, e.g., 70:1 to about 700:1. If the catalyst is used in hydrocarbon conversion processes where acid catalyzed reactions are not desired, e.g., zeolite L reforming, the first zeolite will preferably exhibit reduced acid activity and, more preferably will exhibit little or no acid activity. For these types of processes, the acid activity can be reduced by using high silica to alumina mole ratios, by ion exchange or by other techniques known to persons skilled in the art.

The structure type of the first zeolite will depend on the particular hydrocarbon process in which the zeolite catalyst system is utilized. For instance, if the catalyst is used for the reforming of naphtha to aromatics, the zeolite type will preferably be LTL (example Zeolite L). If the catalyst is be used for xylene isomerization, the first zeolite will preferably be an intermediate pore size zeolite, such as a MFI structure type (example ZSM-5). If the catalyst is used for cracking paraffins, the preferred pore size and structure type will depend on the size of the molecules to be cracked and the desired product. The selection of the structure type for hydrocarbon conversion processes is known to persons skilled in the art.

When the first zeolite is a LTL structure type, the zeolite is preferably an aluminosilicate zeolite having a composition (expressed in terms of molar ratios of the constituent oxides in anhydrous form) of:

$$(0.9-1.3)M_{2/n}O:Al_2O_3:xSiO_2$$

wherein M is a cation of valence n, x is from 4 to 7.5, preferably from 5 to 7.5.

When the zeolite bound zeolite catalyst is used for the isomerization of a feedstream containing alkylaromatic hydrocarbons, the first zeolite is preferably an aluminosilicate zeolite or a gallium silicate zeolite and the zeolite will usually having a silica to alumina mole ratio from 70:1 to 700:1 or a silica to gallia mole ratio from 24 to 500.

The term "average particle size" as used herein, means the arithmetic average of the diameter distribution of the crystals on a volume basis.

The average particle size of the crystals of the first zeolite is preferably from about 0.1 to about 15 microns. In some applications, the average particle size will preferably be at least about 1 to about 6 microns. In other applications such as the cracking of hydrocarbons, the preferred average particle size is smaller, e.g., from about 0.1 to about 3.0 microns.

The structure type of the second zeolite can be the same or can be different from the first zeolite. The structure type of the second zeolite will depend on the intended use of the zeolite bound zeolite catalyst. For instance, if the catalyst system is to be tailored to be a bifunctional catalyst, the first zeolite and second zeolite can be selected and tailored to perform the desired reactions.

When the second zeolite is aluminosilicate zeolite, the silica to alumina mole ratio of the second zeolite, will usually depend upon the structure type of the second zeolite and particular hydrocarbon process in which the catalyst is utilized and is therefore not limited to any particular ratio.

Generally, however, and depending on the structure type of the zeolite, the silica to alumina ratio will be at least 2:1 to greater than 1000. In certain applications, it is desirable that the second zeolite have reduced acidity or even substantially no acidity. In those applications when the zeolite is an intermediate pore size zeolite, such as a ZSM-5, the second zeolite will usually have a silica to alumina mole ratio of 200:1 or greater, e.g., 300:1, 500:1, 1,000:1, etc. In certain applications, the second zeolite will be a Silicalite i.e., a MFI structure type substantially free of aluminia or Silicalite 2, i.e., a MEL structure type substantially free of aluminia. The pore size of the second zeolite will preferably be a pore size that does not adversely restrict access of the desired molecules of the hydrocarbon feedstream to the pores of the first zeolite. For instance, when the material of the feedstream which are to be converted by the first zeolite have a size from 5 Å to 6.8 Å, the second zeolite will preferably be a large pore zeolite or a medium pore zeolite. The second zeolite is usually present in the catalyst system in an amount in the range of from about 10 to 60% by weight based on the weight of the first zeolite by the amount of second zeolite present will usually depend on the hydrocarbon process in which the catalyst is utilized. More preferably the amount of second zeolite present is from about 20 to about 50% by weight.

The second zeolite crystals usually have a smaller size than the first zeolite particles and preferably have an average particle size of less than 1 micron, for example, from about 0.1 to about 0.5 micron. The second zeolite crystals, bind the first zeolite crystals and preferably intergrow and form an over-growth which coats or partially coats the first zeolite. Preferably, the coating is resistant to attrition.

The zeolite bound zeolite catalyst will contain a hydrogenation/dehydrogenation metal. Reference to the hydrogenation/dehydrogenation metal or metals is intended to encompass such metal or metals in the elemental state (i.e. zero valent) or in some other catalytically active form such as an oxide, sulfide, halide, carboxylate and the like. Such metals are known to persons skilled in the art and include, for example, one or more metals, and metals of Groups IIIA, IVA, VA, VIA, VIIA, VIII, IB, IIB, IIIB, IVB, and VB of the Periodic Table of the Elements. Examples of suitable metals include Group VIII metals (i.e., Pt. Pd, Ir, Rh, Os, Ru, Ni, Co and Fe), Group IVA metals (i.e., Sn and Pb), Group VB metals (i.e., Sb and Bi), and Group VIIB metals (i.e., Mn, Tc and Re). Noble metals (i.e., Pt, Pd, Ir, Rh, Os and Ru) are sometimes preferred.

The amount of metal present in the zeolite bound zeolite catalyst will be an effective amount which will generally be from about 0.001 to about 10 percent by weight and, preferably 0.05 to 3.0 percent by weight. The amount will vary with the nature of the metal, less of the highly active metals, particularly platinum, being required than of the less active metals.

In preparing the zeolite bound zeolite catalyst containing the hydrogenation/dehydrogenation metal, the metal will be present in a silica bound aggregate containing the first zeolite prior to converting the silica binder to the second zeolite of the zeolite bound zeolite catalyst. The addition of the metal to the silica bound aggregate can be accomplished at any stage prior to converting the silica binder to the second zeolite such as before, during, or after the formation of the silica bound aggregate.

For example, the zeolite bound zeolite catalyst is preferably made using the following steps:

1. Prepare the first zeolite using known procedures.
2. Form an extrudate mass containing silica and the first zeolite.
3. Extrudate the mass to form a silica bound aggregate.
4. Calcine the silica bound aggregate.
5. Age the silica bound aggregate in an appropriate aqueous solution.
6. Convert the silica binder of the silica bound aggregate to the second zeolite by aging.

The addition of the metal to the silica bound aggregate can take place at any time prior to step 6, e.g., during steps 1–5. For example, the metal can be incorporated with the first zeolite prior to the commencement of step 2 by co-crystallization of the metal and the first zeolite or by loading metal on first zeolite by techniques such as ion exchange or impregnation. The metal can also be added during the formation of the extrudate mass, after formation of the silica bound aggregate, prior to calcination, after calcination, or during the aging of the silica bound aggregate. In a preferred embodiment, the metal is added during step 2 by including the metal in the extrudable mass. After converting the silica binder to the second zeolite, the metal can be present on the surface of either or both zeolites and may also be present in the intracrystalline matrix of either or both zeolites.

Catalysts produced by the method of the invention offer at least one of the following advantages: Improved metal dispersion, reduced cracking activity while maintaining high hydrogenation/dehydrogenation activity, or combinations thereof.

The zeolite bound zeolite catalyst containing the hydrogenation/dehydrogenation metal is preferably prepared by a three step procedure. The first step involves the synthesis of the intermediate pore size first zeolite. Process for preparing the first zeolite are known to persons skilled in the art. For example, with respect to the preparation of an aluminosilicate zeolite or a gallium silicate zeolite having a MFI structure type, one process comprises preparing a solution containing tetrapropyl ammonium hydroxide or bromide, alkali metal oxide, an oxide of aluminum or an oxide of gallium, an oxide of silicon and water, heating the reaction mixture to a temperature of 80° C. to 200° C. for a period of from about four hours to eight days. The resulting gel forms solid crystal particles which are separated from the reaction medium, washed with water and dried. The resulting product can be calcined in air at temperatures of 400° C.–550° C. for a period of 10–40 hours to remove tetrapropylammonium TPA) cations.

In the second step, a silica-bound zeolite is prepared by mixing a mixture comprising the first zeolite crystals, a silica gel or sol, water, and the hydrogenation/dehydrogenation metal or a compound containing the metal, and optionally an extrusion aid, until a homogeneous composition in the form of an extrudable paste develops. The silica used in preparing the silica bound zeolite aggregate is preferably a silica sol and can contain various amounts of trivalent elements, e.g., aluminum or gallium. The amount of silica used is such that the content of the zeolite in the dried extrudate at this stage will range from about 40 to 90% by weight, more preferably from about 50 to 80% by weight, with the balance being primarily silica, e.g. about 20 to 50% by weight silica.

The resulting paste is then molded, e.g., extruded, and cut into small strands, e.g., approximately 2 mm diameter extrudates, which are dried at 100° C. to 150° C. for a period of 4–12 hours and then are calcined in air at a temperature of from about 400° C. to 550° C. for a period of from about 1 to 10 hours.

Optionally, the silica-bound aggregate can be made into very small particles which have application in fluid bed processes such as catalytic cracking. This preferably involves mixing the zeolite with a silica and metal containing matrix solution so that an aqueous solution of zeolite and silica binder is formed which can be sprayed dried to result in small fluidizable silica-bound aggregate particles. Procedures for preparing such aggregate particles are known to persons skilled in the art. An example of such a procedure is described by Scherzer (Octane-Enhancing Zeolitic FCC Catalysts, Julius Scherzer, Marcel Dekker, Inc. New York, 1990). The fluidizable silica-bound aggregate particles, like the silica bound extrudates described above, would then undergo the final step described below to convert the silica binder to a second zeolite.

The final step in the three step catalyst preparation process is the conversion of the silica present in the silica-bound zeolite to a second zeolite which binds the first zeolite crystals together.

To prepare the second zeolite, the silica-bound aggregate is first aged in an appropriate aqueous solution at elevated temperature. Next, the contents of the solution and the temperature at which the aggregate is aged are selected to convert the amorphous silica binder into the desired second zeolite. The newly-formed second zeolite is produced as crystals. The crystals may grow on and/or adhere to the first zeolite crystals, and may also be produced in the form of new intergrown crystals, which are generally much smaller than the first crystals, e.g., of sub-micron size. These newly formed crystals may grow together and interconnect.

The nature of the zeolite formed in the second synthesis conversion of the silica to zeolite may vary as a function of the composition of the secondary synthesis solution and synthesis aging conditions. The secondary synthesis solution is preferably an aqueous ionic solution containing a source of hydroxy ions sufficient to covert the silica to the desired zeolite. It is important, however, that the aging solution be of a composition which will not cause the silica present in the bound zeolite extrudate to dissolve out of the extrudate.

In a preferred embodiment of the invention, the aqueous ionic solution in which the silica bound aggregate is aged contains a source of hydroxy ions (Preferably NaOH). When manufacturing an MFI structure type zeolite, the initial molar ratio of OH to $SiO_2$ is preferably at a level of up to about 1.2, more preferably from about 0.05 to 1.2, and most preferably from about 0.07 to 0.15. This treatment causes the silica binder to be converted substantially to a MFI structure type zeolite, but of lower acidity as reflected by having a significantly higher silica to alumina ratio. The solution also contains a template (e.g., source of tetraalkyl ammonium ions for MFI structure type zeolite) and may optionally include a source of alumina and a source of $Na^+$ ions. The silica to alumina ratio of the converted binder is thus controlled by controlling the composition of the aqueous solution.

It important that the aging solution have a pH which is not too alkaline. This may be achieved, when producing a MFI structure type bound zeolite, by using a solution having an initial molar ratio of $OH:SiO_2$ of 0.05 to 1.2. Generally, ratios of 0.07 to 0.15 are preferred. Aging of the zeolite extrudate in the aging solution is preferably conducted at elevated temperatures, generally in the range of from about 95 to 200° C., more preferably in the range of about 130 to 170° C., most preferably in the range of about 145 to 155° C. Aging time may range from about 20 to 140 hours, more preferably from about 60 to 140 hours, most preferably from about 70 to 80 hours. After aging, the zeolite bound zeolite is separated from solution, washed, dried and calcined.

The first and second zeoltes of the zeoidte catalyst of the present invention may be further ion exchanged as is known in the art either to replace at least in part the original alkali metal present in the zeolite with a different cation, e.g. a Group 1B to VIII Periodic Table of Elements, or to provide a more acidic form of the zeolites by exchange of alkali metal with intermediate ammonium, followed by calcination of the ammonium form to provide the acidic hydrogen form. The acidic form may be readily prepared by ion exchange using a suitable acidic reagent such as ammonium nitrate. The zeolite catalyst may then be calcined at a temperature of 400–550° C. for a period of 10–45 hours to remove ammonia and form the acidic hydrogen form. Ion exchange is preferably conducted after formation of the zeolite catalyst.

The zeolite bound zeolite catalysts of the present invention can be used in processing hydrocarbon feedstocks. Hydrocarbon feed-stocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbon feed is to undergo, the feed can contain metal or can be free of metals. Also, the feed can also have high or low nitrogen or sulfur impurities.

The conversion of hydrocarbon feeds can take place in any convenient mode, for example, in fluidized bed, moving bed, or fixed bed reactors depending on the types of process desired.

The zeolite bound zeolite catalyst can be used as a catalyst for a variety of organic, e.g., hydrocarbon compound conversion processes including hydrogenation, dehydrogenation, dehydrocycization, isomerization, hydrocracking, dewaxing, reforming, conversion of alkyl aromatics, oxidation, reforming, synthesis gas conversion, hydroformylation, dimerization, polymerization, alcohol conversion, etc.

Catalytic conversion conditions for hydrogenation of feedstocks such as alkenes, dienes, polyenes, alkynes, cyclenes, aromatics, oxygenates, etc. include a temperature of between about 0° F. and about 1000° F., preferably between about 80° F. and 900° F., a pressure of between about 10 psia and about 1000 psia, preferably between about 20 psia and 200 psia, a hydrogen/feed mole ratio of between about 0.1 and 20, preferably between about 4 and 12 and a LHSV of between about 0.1 and 20, preferably between about 0.5 and 4.

Dehydrogenation conditions, for processes such as conversion of paraffins to the corresponding olefins, or ethyl benzene to styrene, optionally in the presence of steam or inert gases such as nitrogen, include temperatures of from about 400° F. to 1800° F., preferably from about 650° F. to 1000° F.; feedstock partial pressures of from about 10,000–1500 psia, preferably from about 2 psia to 20 psia and a LHSV of from about 0.1 to 100, preferably between about 0.5 and 4.

Dehydrocyclization conditions, for example for conversion of paraffins to aromatics (e.g., octane to ethylbenzene or xylene), include temperatures of from about 400° F. to 1800° F., preferably from about 600° F. to 1100° F.; feedstock partial pressures of from about 1 psia to 1500 psia, preferably from about 2 psia to 20 psia) and a LHSV of from about 0.1 to 100, preferably between about 0.5 and 4.

Isomerization of normal paraffins, with or without hydrogen, is conducted at a temperature of between about 212° F. and 50° F., preferably between about 400° F. and 900° F., a LHSV of between about 0.01 and 20, preferably between about 0.25 and 5 and a hydrogen to hydrocarbon mole ratio of between 0 and 5:1.

Catalytic conversion conditions for cracking, with or without hydrogen, include a temperature of between about 1200° F. and about 100° F., a pressure of between about 25 psia and about 2500 psia, a hydrogen/feed mole ratio of between about 0 and about 80 and a LHSV of between about 0.1 and about 10.

The catalysts of the present invention are also useful in dewaxing operations. Likewise, the invention can be used in reforming catalysts or as part of a reforming catalyst. Dewaxing and reforming can be carried out in the presence or absence of hydrogen under conditions which include a temperature of from about 500° F. to 1100° F., preferably from about 800° F. to 950° F.; a pressure of from 1.5 psia to 1470 psia and a WHSV of from about 0.01 to about 100, preferably from about 0.1 to 10.

Thus, exemplary hydrocarbon conversion processes which find particular application include the following:

(A) The catalytic cracking of a naphtha feed to produce light olefins. Exemplary reaction conditions include from about 500° C. to about 750° C., pressures of subatmospheric or atmospheric, generally ranging up to about 10 atmospheres (gauge) and residence time (volume of the catalyst feed rate) from about 10 milliseconds to about 10 seconds.

(B) The catalytic cracking of high molecular weight hydrocarbons to lower molecular weight hydrocarbons. Exemplary reaction conditions for catalytic cracking include temperatures of from about 400° C. to about 700° C., pressures of from about 0.1 atmosphere (bar) to about 30 atmospheres, and weight hourly space velocities of from about 0.1 to about 100 $hr^{-1}$.

(C) The isomerization of aromatic (e.g., xylene) feedstock components. Exemplary reaction conditions for such include a temperature of from about 230° C. to about 510° C., a pressure of from about 0.5 atmospheres to about 50 atmospheres, a weight hourly space velocity of from about 0.1 to about 200 and a hydrogen/hydrocarbon mole ratio of from about 0 to about 100.

(D) The hydrocracking of heavy petroleum feedstocks, cyclic stocks, and other hydrocrack charge stocks. The zeolite catalyst system will contain an effective amount of at least one hydrogenation component of the type employed in hydrocracking catalysts.

(E) The conversion of light paraffins to olefins and/or aromatics. Exemplary reaction conditions include temperatures from about 425° C. to about 760° C. and pressures from about 10 to about 2000 psig.

(F) The conversion of light olefins to gasoline, distillate and lube range hydrocarbons. Exemplary reaction conditions include temperatures of from about 175° C. to about 375° C. and a pressure of from about 100 to about 2000 psig.

(G) Two-stage hydrocracking for upgrading hydrocarbon streams having initial boiling points above about 200° C. to premium distillate and gasoline boiling range products or as feed to further fuels or chemicals processing steps. The first stage would be the zeolite catalyst comprising one or more catalytically active metals, e.g., a Group VIII metal, and the effluent from the first stage would be reacted in a second stage using a second zeolite, e.g., zeolite Beta, comprising one or more catalytically active substances, e.g., a Group VIII metal, as the catalyst. Exemplary reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(H) A combination hydrocracking/dewaxing process in the presence of the zeolite bound zeolite catalyst comprising a hydrogenation component and a zeolite such as zeolite Beta. Exemplary reaction conditions include temperatures from about 350° C. to about 400° C., pressures from about 1400 to about 1500 psig, LHSVs from about 0.4 to about 0.6 and a hydrogen circulation from about 3000 to about 5000 SCF/bbl.

(I) The reaction of alcohols with olefins to provide mixed ethers, e.g., the reaction of methanol with isobutene and/or isopentene to provide methyl-t-butyl ether (MTBE) and/or t-amyl methyl ether (TAME). Exemplary conversion conditions include temperatures from about 20° C. to about 200° C., pressures from 2 to about 200 atm, WHSV (gram-olefin per hour gram-zeolite) from about 0.1 $hr^{-1}$ to about 200 $hr^{-1}$ and an alcohol to olefin molar feed ratio from about 0.1/1 to about 5/1.

(J) The conversion of naphtha (e.g., $C_6$–$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 40 bar, and liquid hourly space velocities (LHSV) ranging from 0.1 to 15.

(K) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100;

(L) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a zeolite bound zeolite at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the zeolite bound zeolite catalyst. Thus, when the olefin feedstock contacts the catalyst in the liquid phase, temperatures of from about 10° C. to about 250° C. may be used.

(M) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

(N) The conversion of alkylaromatic hydrocarbons such as the dealkylation of ethylbenzene to benzene.

(O) The saturation of olefins having from 2 to 20 carbon atoms.

(P) The isomerization of ethylbenzene to xylenes. Exemplary conversion conditions include a temperature from 600°–800° F., a pressure of from 50 to about 500 psig and a LHSV of from about 1 to about 10.

In general, the, catalytic conversion conditions over the zeolite catalyst of the invention independently and in combination include a temperature of from about 100° C. to about 760° C., a pressure of from about 0.1 atmosphere (bar) to about 200 atmospheres (bar), a weight hourly space velocity of from about 0.08 hr$^{-1}$ to about 2,000 hr$^{-1}$.

Although many hydrocarbon conversion processes prefer that the second zeolite crystals have lower acidity, some processes prefer that the second zeolite crystals have higher acidity.

Processes that find particular application using the zeolite bound zeolite catalyst are those where two or more reactions are taking place within the zeolite catalyst system. The zeolite bound zeolite catalyst would comprise two different zeolites that are each separately tailored to promote or inhibit different reactions. A process using such a catalyst benefits not only from greater apparent catalyst activity, greater zeolite accessibility, and reduced non-selective surface acidity possible with zeolite bound zeolites, but from a tailored catalyst system.

The zeolite bound zeolite catalyst finds particular application for isomerizing one or more xylene isomers in a $C_8$ aromatic feed containing ethylbenze to obtain ortho-, meta-, and para-xylene in a ratio approaching the equilibrium value while substantially converting ethylbenzene. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. At the same time, it is also desirable that ethylbenzene in the feed be converted with very little net loss of xylenes. The acidity of the first zeolite and second zeolite of the zeolite bound zeolite catalyst can be selected to balance xylene isomerization and ethylbenzene dealkylation while minimizing undesirable side reactions, e.g., ethylation of xylenes and ethylbenzene/ethylbenzene or ethylbenzene/xylene transalkylation. The isomerization process is carried out by contacting a $C_8$ aromatic stream containing one or more xylene isomers or ethylbenzene or mixtures thereof, under isomerization conditions with the zeolite bound zeolite catalyst. The catalyst of the present invention is useful in saturating ethylene formed during ethylbenzene dealkylation and offers the benefit of reduced aromatics saturation and subsequent cracking of naphthenes.

Suitable isomerization conditions include a temperature in the range of 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 0.1 to 30.0 moles of hydrogen per mole of alkylbenzene. If hydrogen is used, the catalyst should comprise 0.1 to 2.0 wt. % of a hydrogenation/dehydrogenation component selected from Group VIIIA of the Periodic Table, especially platinum, palladium, or nickel. By Group VIII metal component is meant that the metals or their compounds such as oxides and sulfides.

The zeolite bound zeolite catalysts find particular application in reactions involving aromatization and/or dehydrogenation. They are particularly useful in a process for the dehydrocyclization and/or isomerization of acyclic hydrocarbons in which the hydrocarbons are contacted at a temperature of from 370° C. to 600° C., preferably from 430° C. to 550° C. with the zeolite bound zeolite catalyst, preferably zeolite L bound by zeolite L, preferably having at least 90% of the exchangeable cations as alkali metal ions and incorporating at least one Group VIII metal having dehydrogenating activity, so as to convert at least part of the acyclic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbon such as methylcyclopentane may also be used. In a preferred embodiment, the feed to a process for preparing aromatic hydrocarbons and particularly benzene comprises hexanes. The temperature of the catalytic reaction may be from 370° C. to 600° C., preferably 430° C. to 550° C. and preferably pressures in excess of atmospheric are used, for example up to 2000 KPa, more preferably 500 to 1000 KPa. Hydrogen is usually employed in the formation of aromatic hydrocarbons preferably with a hydrogen to feed ratio of less than 10. The following examples illustrate the invention:

EXAMPLE 1
Preparation of Zeolite Bound MFI Type Gallium Silicate Catalyst

I. Catalyst A—Platinum Loaded During Synthesis

MFI structure gallium silicate crystals were prepared as follows:

| Components Use for Preparation | Quantity (Grams) |
|---|---|
| Solution A | |
| NaOH pellets (98.6%) | 18.82 |
| $Ga_2O_3$ (99.999%) | 12.06 |
| Water | 50.08 |
| Rinse Water | 189.80 |
| Solution B | |
| Colloidal Silica (Ludox HS-40) | 773.06 |
| Solution C | |
| Tetrapropylammonium bromide | 123.73 |
| Water | 425.01 |
| Rinse Water | 124.97 |
| Solution D | |
| Aqueous Suspension of Colloidal Silicalite with 0.0794 wt. % Seeds | 2.39 |
| Rinse Water | 100.00 |

The ingredients of Solution A were dissolved by boiling until a clear solution was obtained. Solution A was then cooled to ambient temperature and water loss from boiling was corrected.

Solution B was poured into a 2 liter glass beaker. Solution C was poured into the contents of the beaker and mixed. Solution D was then poured into the contents of the beaker and the beaker content was mixed. The contents of the beaker were poured into a 2 liter stainless steel autoclave. Rinse Water was used to rinse the beaker and added to the autoclave. Solution A were added to the autoclave. The contents of the autoclave were mixed about 20 minutes. A smooth pourable gel was obtained. The gel had the following composition expressed in moles of pure oxide:

0.45 $Na_2O$/0.90 TPA Br/0.125 $Ga_2O_3$/10$SiO_2$/147 $H_2O$

The gel contained 1.0 wt ppm of colloidal silicalite seeds.

The autoclave was placed in an oven and heated to 150° C. in 2 hours and maintained at 150° C. at this temperature for 48 hours.

The product was removed from the autoclave and divided into 3 portions. Each portion was washed 7 times with about 600 grams of water. The product was dried over night at 120° C. The amount of product recovered was 333.70 grams. The product was calcined in air at 475° C. for 48 hours. The characteristics of the calcined product were the following:

XRD: Pure MFI

SEM: 4 micron size spherical crystals

Elemental: $SiO_2/Ga_2O_3=80$

A portion of the calcined product was formed into silica bound 2 mm extrudates as follows:

| Components Used for Preparation | Quantity Grams |
|---|---|
| Silica Sol (Nyacol 2034 DI) | 128.59 |
| Silica gel (aerosil 300) | 12.26 |
| $H_2PtCl_6.6H_2O$ | 2.47 |
| Water | 35.01 |
| Rinse Water | 3.00 |
| Gallium silicate MFI Crystals | 130.00 |
| Extrusion Aid (hydroxypropyl methyl cellulose) | 0.87 |

The components were mixed in a food mixer in the order shown. After adding the extrusion aid and mixing for about 7 minutes, a thick and smooth paste was obtained. The paste was extruded into 2 mm extrudates and dried at ambient temperature for 3 hours. The extrudates were broken into smaller 5 mm pieces and dried in an oven at 120° C. for 16 hours. The dried extrudates were calcined at 490° C. for 8 hours in air.

Composition of calcined silica bound extrudate:

Silica binder: 30.1 wt. %

MFI: 69.4 wt. %

Platinum 0.5 wt. %

The silica bound extrudates were converted into zeolite bound zeolite as follows:

| Components Used for Preparation | Quantity (Grams) |
|---|---|
| Solution A | |
| NaOH pellets (98.6%) | 1.36 |
| Water | 29.08 |
| Rinse Water | 11.78 |
| Solution B | |
| Tetrapropylammonium bromide | 9.28 |
| Water | 30.35 |
| Rinse Water | 22.16 |

Solutions A and B were poured into a 1 liter autoclave and mixed. Finally, 70.0 grams of the silica bound extrudates were added to the autoclave. The molar composition of the synthesis mixture was:

The autoclave was placed into an oven. The oven was heated from room temperature to 150° C. in 2 hours and maintained at this temperature for 80 hours. The resulting product was washed at 60° C. 4 times with 1700 ml of water. The conductivity of the last wash water was 49 $\mu$S/cm. The extrudates were dried at 120° C. and calcined in air at 490° C. for 16 hours.

The product was analyzed by XRD and SEM with the following results:

XRD: Excellent crystallinity

SEM: 4 micron size crystals coated with smaller size crystals. No visible amorphous silica.

Elemental:
Core crystals: $S_iO_2/Ga_2O_3=80$
Binder crystals=silicalite
Core crystals=70 wt. %
Platinum=0.5 wt. %

Platinum distribution and platinum particle size were determined by qualitatively examining a sample of the product by transmission electron microscopy (TEM) using a Philips CM12 TEM. FIG. 1 represents an electron micrograph of the Catalyst A. The images of the micrograph indicate that platinum was distributed well. The major proportion of the platinum had a particle size of 5–10 nm.

II. Catalyst B—Platinum Loaded by Pore Filling

A portion of the calcined MFI structure type gallium silicate used to prepare Catalyst A was formed into silica bound 2 mm extrudates as follows:

| Components Used for Preparation | Quantity (Grams) |
|---|---|
| Gallium-silicate MFI crystals | 130.05 |
| Water | 37.70 |
| $SiO_2$ gel (aerosil 300) | 45.26 |
| Silica Sol (NALCOAG 1034A) | 128.57 |
| Extrusion aid (hydroxypropyl methyl cellulose) | 0.89 |

The above components were mixed in a food mixer in the order shown. After adding the extrusion aid and mixing for about 14 minutes, a thick and smooth paste was obtained. The paste was extruded into 2 mm extrudates. The extrudates were dried at 150° C. for 7 hours and then calcined in air at 510° C. for 8 hours.

Composition of calcined silica-bound extrudates:

MFI: 70.0 wt. %

$S_iO_2$ binder: 30.0 wt. %

The silica bound extrudates were converted into zeolite bound zeolite as follows:

| Components Used for Preparation | Quantity (Grams) |
|---|---|
| Solution A | |
| NaOH pellets (98.6%) | 2.44 |
| Water | 51.91 |
| Rinse Water | 21.08 |
| Solution B | |
| Tetrapropylammonium bromide | 16.56 |
| Water | 54.20 |
| Rinse Water | 39.54 |

Solution A and B were poured into a 300 ml stainless steel autoclave and were mixed. Finally, 125.00 grams of the silica-bound MFI extrudates were added to the autoclave. The molar composition of the synthesis mixture was:

In this mixture, the silica is present as the binder in the extrudate.

The autoclave was placed into an oven at room temperature, heated to 150° C. within 2 hours, and maintained at 150° C. for 72 hours. The resulting product was washed at 60° C. with 7 portions of 2000 ml of water. The conductivity of the last wash water was 25 $\mu$S/cm. The product was dried at 150° C. and calcined in air at 500° C. for 16 hours.

The resulting product was characterized by x-ray diffraction (XRD) and scanning electron microscopy (SEND with the following results:

XRD: Excellent crystallinity

SEM: 4 micron MFI crystals coated with smaller size crystals. No visible amorphous silica.

Elemental:
 Core crystals: $S_iO_2/Ga_2O_3=80$
 Binder crystals=silicalite
 Core crystals=70 wt. %
 Binder crystals=30 wt. %

An amount of 0.31 wt. % of platinum (based on the weight of product) was loaded into the catalyst. The process was carried out by first exchanging the catalyst at 65° C. with a 1 normal $NH_4Cl$ solution. The exchanged catalyst was washed with water, dried, and then calcined at 530° C. for 8 hours. The loading of the platinum was done by the pore-filling method with an appropriate amount of $Pt(NH_3)_4Cl_2$ dissolved in water. After loading, the catalyst was dried and calcined at 480° C. for 8 hours.

Figure 2:
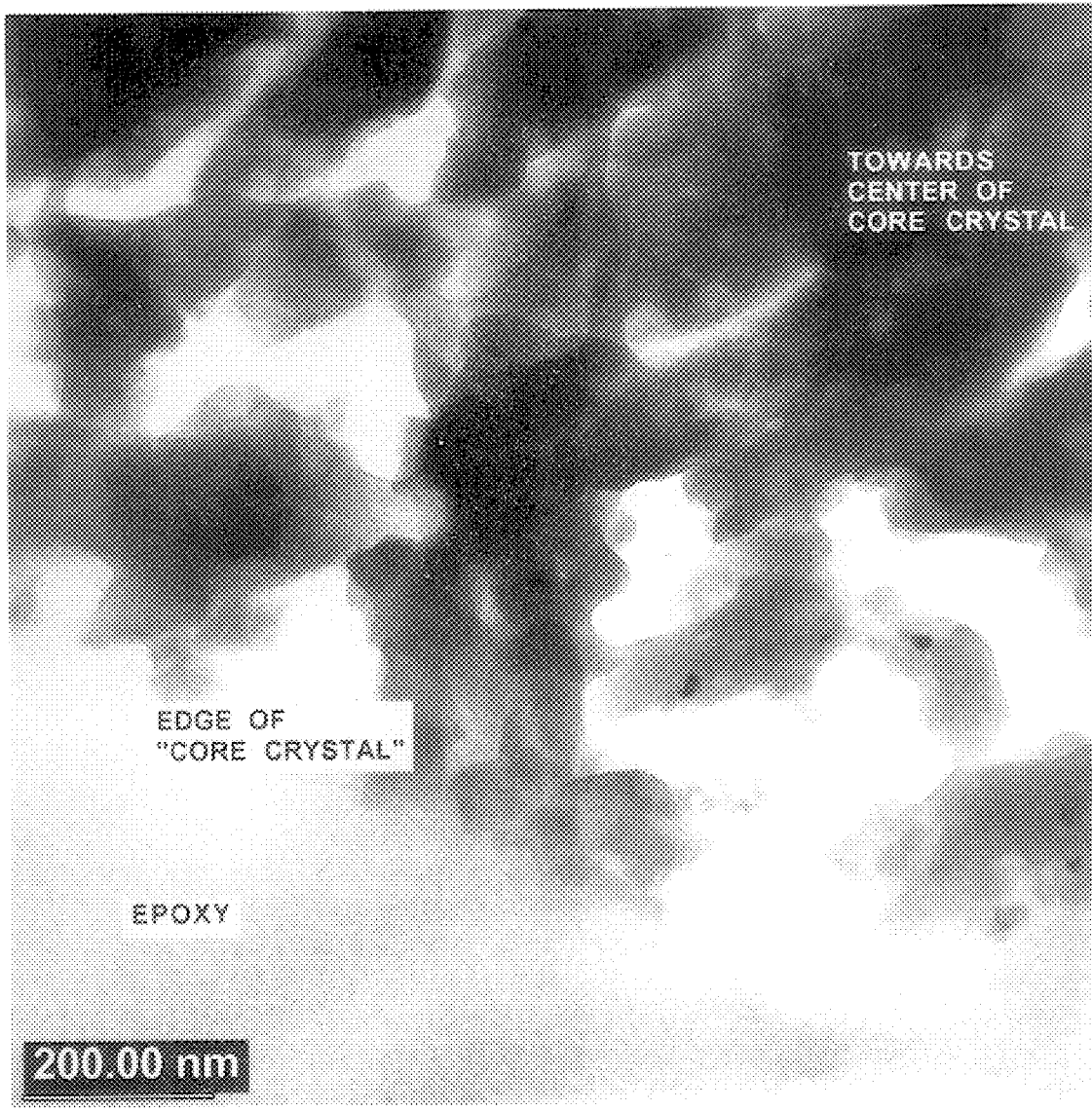
FIG. 2 represents an electron micrograph of the catalyst prepared in Example 1.II.

Platinum distribution and platinum particle size were determined by qualitatively examining a sample of the product by transmission electron microscopy (TEM) using a Philips C12 TEM. FIG. 2 represents an electron micrograph of Catalyst B. The images of the micrograph indicate that the platinum particle size was predominantly 10–30 nm and platinum was not as well distributed as Catalyst A.

EXAMPLE 2

I. Catalyst A—Combined Xylene Isomerization/Ethylbenzene Dealkylation Tests

A series of combined xylene isomerization/ethylbenzene dealkylation tests were conducted using Catalyst A by passing an xylenes rich feed through a fixed bed reactor. Catalyst A was pretreated in $H_2$ for two (2) hours at 850° F. and 250 psig. After the temperature had been lowered to 700° F., the catalyst was presulfided to breakthrough with about 500 ppm $H_2S$ in $H_2$ at 250 psig. The subsequent on-oil tests were run at varying conditions. The conditions and results are shown in Table I below:

TABLE I

| | Run No. | | | | |
|---|---|---|---|---|---|
| | 1 | 2 | 3 | 4 | 5 |
| Temperature (°F.) | 750 | 750 | 750 | 795 | 750 |
| HC Partial Pressure (inlet) | 163 | 118 | 118 | 118 | 163 |
| $H_2$ Partial Pressure (inlet) | 81 | 118 | 118 | 118 | 81 |
| WHSV (#/#/Hr) | 10 | 3.7 | 10 | 20 | 10 |
| $H_2$:Oil Ratio (Molar) | 0.5 | 1.0 | 1.0 | 1.0 | 0.5 |
| Hours On-Oil | 155 | 431 | 481 | 621 | 748 |
| Feed EB Wt.% | 11.4 | 12.6 | 12.6 | 12.6 | 12.6 |
| Feed Xylenes Wt. % | 86.8 | 85.3 | 85.3 | 85.3 | 85.3 |
| Feed PX Wt. % | 2.7 | 1.1 | 1.1 | 1.1 | 1.1 |
| % EB reacted | 73.7 | 93.5 | 73.0 | 74.3 | 74.7 |
| Ring Loss (% of feed | 0.1 | *–0.1 | *–0.1 | *–0.2 | *–0.2 |

TABLE I-continued

| | Run No. | | | | |
|---|---|---|---|---|---|
| | 1 | 2 | 3 | 4 | 5 |
| aromatic rings) | | | | | |
| Xylenes Loss (% of feed xylenes) | 2.0 | 5.9 | 2.3 | 2.5 | 2.5 |
| PX approach to equilibrium (%) | 103 | 101 | 101 | 98 | 100 |

*Negative values believed due to minor gas chromatography variations.

The percent, % EB reacted was determined by the formula: % EB Conv=100×(moles of EB in feed–moles of EB in product)/(moles of EB in feed); Aromatics ring loss % was determined by the formula: 100 ×(moles of aromatics in feed–moles of aromatics in product)/(moles of aromatics in feed). Loss of xylenes was determined by the formula: 100×(moles of xylenes in feed–moles of xylenes in product)/(moles of xylenes in feed) and PX approach to equilibrium was determined by the formula: (Product PX/Xs–Feed PX/Xs)/(Equilibrium PX/Xs–Feed PX/Xs) X100.

II. Catalyst B—Combined Xylene Isomerization/Ethylbenzene Dealkylation Tests

A series of combined xylene isomerization/ethylbenzene dealkylation tests were conducted using Catalyst B by passing an artificial feed through a fixed bed reactor. Catalyst B was pretreated in $H_2$ and presulfided using the same procedure described in Example II. The subsequent on-oil tests were run at varying conditions. The conditions and results are shown in Table II below:

TABLE II

| | Run No. | | | | |
|---|---|---|---|---|---|
| | 1 | 2 | 3 | 4 | 5 |
| Temperature (°F.) | 736 | 750 | 710 | 786 | 736 |
| HC Partial Pressure | 163 | 118 | 118 | 118 | 118 |
| $H_2$ Partial Pressure | 81 | 118 | 118 | 118 | 118 |
| WHSV (#/#/Hr) | 10 | 10 | 5 | 20 | 10 |
| $H_2$:Oil Ratio (Molar) | 0.5 | 1.0 | 1.0 | 1.0 | 1.0 |
| Hours On-Oil | 160 | 233 | 633 | 656 | 714 |
| Feed EB Wt. % | 12.3 | 12.6 | 12.6 | 12.6 | 12.6 |
| Feed Xylenes Wt. % | 85.3 | 85.3 | 85.3 | 85.3 | 85.3 |
| Feed PX Wt. % | 7.2 | 1.1 | 1.1 | 1.1 | 1.1 |
| % EB reacted | 72 | 78.3 | 75.8 | 74.0 | 69.4 |
| Ring Loss (% of feed aromatic rings) | 0.1 | 1.3 | 1.2 | 0.6 | 1.0 |
| Xylenes Loss (% of feed xylenes) | 3.3 | 4.2 | 3.7 | 3.4 | 2.9 |
| PX approach to equilibrium (%) | 102 | 101 | 101 | 99 | 101 |

The data in the Tables shows that at comparable ethylbenzene conversion, ring loss and xylene loss for Catalyst A were significantly lower than for Catalyst B. Both Catalyst A and Catalyst were effective in isomerizing xylenes and converting ethylbenzene.

EXAMPLE 3

Preparation of Zeolite KL Bound by Zeolite KL

I. Catalyst C—Platinum Loaded During Synthesis.

LTL structure aluminosilicate crystals (zeolite KL) were prepared as follows:

| Components Use for Preparation | Quantity (Grams) |
|---|---|
| Solution A | |
| KOH pellets (87.0%) | 176.3 |
| Al(OH)$_3$ | 81.7 |
| Water | 837.2 |
| Solution B | |
| Colloidal Silica (Ludox HS-40) | 786.9 |
| Rinse Water | 104.8 |

The ingredients of Solution A were dissolved by boiling until a clear solution was obtained. Solution A was then cooled to ambient temperature and water loss from boiling was corrected.

Solution B was poured into a 2 liter stainless steel autoclave. Solution A was added to the autoclave. Rinse Water was used to rinse the beaker and added to the autoclave. The contents of the autoclave were mixed until a smooth gel was obtained. The gel had the following composition expressed in moles of pure oxide:

$$2.61\ K_2O/1.0\ Al_2O_3/10SiO_2/158\ H_2O$$

The filled autoclave was pressurized to 65 psig with nitrogen gas and then heated in 48 hours to a wall temperature of 79° C. without stirring. The autoclave was then stirred at 20 rpm and heated to a wall temperature of 150° C. in 56 hours. Stirring was stopped and the autoclave was maintained at 150° C. for 56 hours.

The product was removed from the autoclave and washed 3 times with cold demineralized water. The pH of the first wash was 12.3, the Ph of the second wash was 11.7 and the pH of the final wash 11.4. The product was dried over night at 150° C. The amount of product recovered was 310 grams. X ray diffraction analysis showed the dried product was pure zeolite KL.

A portion of the calcined product was formed into silica bound 2 mm extrudates as follows:

| Components Used for Preparation | Quantity (Grams) |
|---|---|
| Silica Sol (Nalcoag 1034A) Zeolite KL Crystals | 124.68 |
| Silica H$_2$O Gel (Aerosil 200) Water | 11.91 |
| H$_2$PtCl$_6$.6H$_2$O | 2.92 |
| H$_2$O | 26.28 |
| Rinse H$_2$O | 9.72 |
| Aluminosilicate LTL crystals (KL) | 126.2 |
| Additional H$_2$O | 3.0 |
| Methocel (Hydroxypropyl methyl cellulose extrusion Acid) | 0.87 |

The above components were mixed in a household mixed in the order shown. After adding the methocel, a thickened and extrudable dough was obtained. The total mixing time was about 30 minutes.

The dough was extruded into 2 mm extrudates, dried for 2 hours at room temperature and then for 16 hours at 120° C., broken into 5mm pieces and then calcined at 490° C. for 5 hours in air. The amount of calcined product recovered was 139.3 grams.

Composition of calcined silica-bound extrudates:

Zeolite KL: 69.5 wt. %

SiO$_2$ Binder: 29.9 wt. %

Platinum: 0.6 wt %

The silica-bound zeolite KL extrudates were converted into zeolite KL bound by zeolite KL as follows:

A potassium aluminate solution was prepared from the following (weight of the chemicals in grams):

KOH pellets, purity 87.3%=8.44

Al(OH)$_3$ powder, purity 98.5%=6.40

H$_2$O=56.65

The alumina was dissolved by boiling until a clear solution was obtained. The solution was cooled to room temperature and corrected for water loss due to boiling. The aluminate solution was quantitatively transferred with 5.92 grams of rinse water into a 300 ml stainless steel autoclave. Next 50.00 grams of silica-bound extrudates containing 29.9 wt. % of silica binder (0.20 grams of adsorbed water in extrudates) were added to the contents of the autoclave. The extrudates had been previously dried to remove adsorbed water. The composition of the mixture in the autoclave, corrected for the water content of the extrudates, was:

$$2.64K_2O/1.62Al_2O_3/10SiO_2/148H_2O$$

In this mixture the silica is present as the binder in the extrudate.

The autoclave was heated up to 175° C. within 4.5 hours and kept at this temperature for 65 hours. After this aging period the autoclave was opened and the product-extrudates were collected.

The extrudates were washed two times with 500 ml of water (temperature 60° C.) and then washed with 250 ml of water (temperature 60° C.). The pH of the final wash water was 10.8 and the conductivity was 321 μS/cm. The extrudates were dried over night at 120° C. The amount of product recovered was 55.8 grams.

The product-extrudates were characterized by XRD and SEM with the following results:

XRD: Indicated the presence of zeolite L

SEM: Showed presence of zeolite L crystals bound by newly formed smaller crystals II. Catalyst D—Platinum Loaded by Pore Filling A portion of the calcined LTL structure type aluminosilicate (zeolite KL) used to prepare Catalyst C was formed into silica bound 2 mm extrudates as follows:

| Components Used for Preparation | Quantity (Grams) |
|---|---|
| Silica Sol (Nalcoag 1034A) | 128.2 |
| Silica H$_2$O Gel (Aerosil 200) | 12.26 |
| Water | 37.06 |
| Zeolite KL Crystals | 130.01 |
| Methocel (Hydroxypropyl methyl cellulose extrusion Acid) | 0.88 |

The above components were mixed in a household mixed in the order shown. After adding the methocel, a thickened and extrudable dough was obtained. The total mixing time was about 18 minutes.

The dough was extruded into 2 mm extrudates, dried for 2 hours at room temperature and then for 16 hours at 120° C., broken into 5 mm pieces and then calcined at 490° C. for 5 hours in air. The amount of calcined product recovered was 147.39 grams.

Composition of silica-bound extrudates:

Zeolite KL: 69.95 wt. %

SiO$_2$ Binder: 30.05 wt. %

The silica-bound zeolite KL extrudates were converted into zeolite KL bound by zeolite KL as follows:

A potassium aluminate solution was prepared from a potassium aluminate solution was prepared from the following (weight of the chemicals in grams):

KOH pellets, purity 87.3%=9.25

Al(OH)$_3$ powder, purity 98.5%=6.43

H$_2$O=56.99

The alumina was dissolved by boiling until a clear solution was obtained. The solution was cooled to room temperature and corrected for water loss due to boiling. The aluminate solution was quantitatively transferred with 5.94 grams of rinse water into a 300 ml stainless steel autoclave. Next 50.0 grams of the silica-bound extrudates containing 30 wt. % of silica binder (0.47 grams of adsorbed water in extrudates) were added to the contents of the autoclave. The extrudates had been previously dried to remove adsorbed water. The composition of the mixture in the autoclave, corrected for the water content of the extrudates, was:

2.88K$_2$O/1.62Al$_2$O$_3$/10SiO$_2$/148H$_2$O

In this mixture the silica is present as the binder in the extrudate.

The autoclave was heated up to 175° C. within 5.5 hours and kept at this temperature for 65 hours. After this aging period the autoclave was opened and the product-extrudates were collected.

The extrudates were washed with 2000 ml of water for 1 hour (temperature 60° C.) and then washed with 1000 ml of water for 2 hours (temperature 60° C.). The pH of the final wash water was 10.8 and the conductivity was 662 μS/cm. The extrudates were dried over night at 120° C. The amount of product recorded was 52.6 grams.

The product-extrudates were characterized by XRD and SEM with the following results:

XRD: Indicated the presence of zeolite L

SEM: Showed presence of zeolite L crystals bound by newly formed smaller crystals An amount of 0.85 wt. % of platinum (based on the weight of catalyst) was loaded into Catalyst D by the pore-filling method with an appropriate amount of Pt (NH$_3$)$_4$Cl$_2$ dissolved in water. After loading, the catalyst was dried.

EXAMPLE 4

Two separate aromatization tests were carried out using Catalyst C and Catalyst D. Prior to start of the tests, each catalyst underwent a redispersion procedure and a reduction procedure as follows:

10 grams of catalyst was loaded in a one inch ID quartz tube that was placed in an electrically heated oven. For all of the treatment steps described gas flowed through the tube and catalyst sample at a flow rate of 500 cc/minute. The catalyst was initially heated to 450° C. with a gas composition of 10 volume percent O$_2$ and 90 volume percent helium. The catalyst was held at 450° C. for one hour. The temperature was then increased to 530° C. and the gas composition changed to 20 volume percent O$_2$, 2.2 volume percent H$_2$O, and 77.8 volume percent helium. The catalyst was exposed to these conditions for 67.5 hours. The catalyst was then cooled to 510° C. in dry helium. At that point, the gas composition was changed to 20 volume percent O$_2$, 2.2 volume percent H$_2$O, and 77.8 volume percent helium. After 30 minutes the gas composition was changed to 0.8 volume percent chlorine, 20 volume percent O$_2$, 2.2 volume percent H$_2$O and 77.0 volume percent helium. The catalyst was exposed to these conditions for 2 hours. The gas composition was then changed to 20 volume percent O$_2$, 2.2 volume percent H$_2$O and 77.8 volume percent helium. After two hours at these conditions the O$_2$ was removed and residual oxygen purged from the reactor with 2.2 volume percent H$_2$O and 97.8 volume percent helium. At that point, hydrogen was introduced to change the gas composition to 20 volume percent H$_2$, 2.2 volume percent H$_2$O and 77.8 volume percent helium. The catalyst was reduced at these conditions for one hour. The gas composition was then changed to dry helium and the catalyst cooled to room temperature and removed from the reactor.

The first aromatization test was carried out at a temperature of 950° F. and 1000 psig pressure with a C$_6$ mixed feed comprising 60% by weight and n-hexane, 30% by weight 3-methylpentane, and 10% by weight methylcyclopentene, at a weight hourly space velocity of 6.0 w/w hr$^{-1}$ and in the presence of hydrogen, the H$_2$:hydrocarbon ratio being 6. The time on stream for Catalyst C was 14.6 hours and Catalyst D was 14.4 hours. The results are set forth in Table 3 below:

TABLE 3

| Product | Catalyst C | Catalyst D |
|---|---|---|
| C$_1$–C$_2$ | 5.8 | 13.5 |
| C$_3$–C$_4$ | 6.6 | 16.6 |
| C$_5$–C$_6$ | 21.3 | 11.0 |
| Benzene | 66.3 | 58.4 |
| Toluene | 0.1 | 0.3 |
| A$_8^+$ | 0.0 | 0.1 |

The data in the Table shows that Catalyst C had 14 percent higher benzene yield than Catalyst D and had more than 50% less undesirable feed stream cracking to C$_1$–C$_4$ products.

The second aromatization test was carried out at a temperature of 860° F. and a 100 psig pressure with a light virgin naphtha feed at a weight hourly space velocity of 1.0 w/w hr 1 and in the presence of hydrogen, the H$_2$:hydrocarbon ration being 6. The time on stream for Catalyst C was 16.5 hours and Catalyst D was 16.3 hours. The composition of the LVN feed comprised:

| Component | Weight % |
|---|---|
| C$_5$ | 0.26 |
| C$_6$ | 5.85 |
| C$_7$ | 18.99 |
| C$_8$ | 22.35 |
| C$_9$ | 21.60 |
| C$_{10}$ | 10.37 |
| C$_{11}$ | 2.93 |
| Benzene | 0.32 |
| Toluene | 3.13 |
| A$_8$ | 5.33 |
| A$_9$ | 8.07 |
| A$_{10}$ | 0.80 |

The results of these tests are set forth below in Table 4.

TABLE 4

| Product | Catalyst C | Catalyst D |
|---|---|---|
| C$_1$–C$_2$ | 7.2 | 12.0 |
| C$_3$–C$_4$ | 3.3 | 3.7 |
| C$_5$–C$_6$ | 30.9 | 20.5 |

TABLE 4-continued

| Product | Catalyst C | Catalyst D |
|---------|-----------|-----------|
| Benzene | 10.0 | 14.3 |
| Toluene | 22.1 | 31.5 |
| $A_8$ | 20.0 | 15.1 |
| $A_9$ | 5.8 | 2.6 |
| $A_{10}$ | 0.6 | 0.3 |

The data in the Table shows that Catalyst C had over 50 percent greater net $A_8$ yield than Catalyst D and also had more than 40% reduction in feed stream cracking to $C_1$–$C_2$. Catalyst D produced more benzene and toluene than Catalyst C but partially at the expense of more desirable xylenes.

What is claimed is:

1. A zeolite bound zeolite hydrocarbon conversion catalyst which does not contain significant amounts of non-zeolitic binder and contains at least one hydrogenation/dehydrogenation metal and comprises:
   (a) first crystals of a first zeolite, and
   (b) a binder comprising second crystals of a second zeolite; and
   (c) an effective amount of at least one hydrogenation/dehydrogenation metal:
wherein said zeolite bound zeolite catalyst is prepared by (i) providing said first crystals of said first zeolite; (ii) forming a silica bound aggregate comprising at least a portion of said at least one hydrogenation/dehydrogenation metal and said first crystals of said first zeolite; and (iii) converting to said second zeolite the silica binder of said silica bound aggregate, wherein said portion of said at least one hydrogenation/dehydrogenation metal is added during the preparation of said zeolite bound zeolite hydrocarbon conversion catalyst after step (i).

2. The catalyst recited in claim 1, wherein said second crystals are intergrown and form at least a partial coating on said first crystals.

3. The catalyst recited in claim 2, wherein said first crystals of said first zeolite have an average particle size greater than about 0.1 micron and said second crystals of said second zeolite have an average particle size that is less than said first crystals of said first zeolite.

4. The catalyst recited in claim 3, wherein said first zeolite is a structure type selected from the group consisting of OFF, BEA, MAZ, MEI, FAU EMT, LTL, VFI, MOR, MFI, MFS, MEL, MTW, MTT, FER, EUO, HEU, TON, CHA, ERI, KFI, LEV, and LTA.

5. The catalyst recited in claim 4, wherein said second zeolite is a structure type selected from the group consisting of OFF, BEA, MAZ, MEI, FAU, EMT, LTL, VFI, MOR, MFI, MFS, MEL, MTW, MTT, FER, EUO, HEU, TON, CHA, ERI, KFI, LEV, and LTA.

6. The catalyst recited in claim 5, wherein said first zeolite and said second zeolite are an aluminosilicate zeolite or a gallium silicate zeolite.

7. The catalyst recited in claim 6, wherein said second zeolite has lower acidity than said first zeolite.

8. The catalyst recited in claim 7, wherein said second crystals are resistant to attrition.

9. The catalyst recited in claim 6, wherein the acidity of said second zeolite is higher that the acidity of said first zeolite.

10. The catalyst recited in claim 6, wherein said first zeolite and said second zeolite have a large pore size or an intermediate pore size.

11. The catalyst recited in claim 6, wherein said first zeolite has a silica to alumina mole ratio of from about 70:1 to about 700:1 or a silica to gallia mole ratio from about 24:1 to about 500:1.

12. The catalyst recited in claim 11, wherein the average particle size of the crystals of said first zeolite is from about 1 to about 6 microns and the average particle size of the crystals of said second zeolite is from about 0.1 to about 0.5. microns.

13. The catalyst recited in claim 6, wherein said catalyst is prepared by aging at elevated temperatures a silica-bound aggregate containing said hydrogenation/dehydrogenation metal and first crystals of said first zeolite in an aqueous ionic solution containing a source of hydroxy ions sufficient to convert the silica binder to the second zeolite.

14. The catalyst recited in claim 13, wherein said zeolite bound zeolite catalyst contains less than 5% by weight of non-zeolitic binder based on weight of said first zeolite and said second zeolite.

15. The catalyst recited in claim 6, wherein said first zeolite and said second zeolite have LTL structure type.

16. The catalyst recited in claim 6, wherein said first zeolite and said second zeolite have a MFI or MEL structure.

17. The catalyst recited in claim 16, wherein said first zeolite has a silica to aluminum mole ratio from 70 to 700 or a silica to gallia mole ratio from 20 to 500.

18. The catalyst recited in claim 17, wherein said second zeolite has a silica to alumina mole ratio greater than 200 or a silica to gallia mole ratio greater than 100.

19. The catalyst recited in claim 6, wherein said at least hydrogenation/dehydrogenation metal comprises a Group VIIIA metal.

20. A process of preparing a hydrogenation/dehydrogenation metal containing-zeolite bound zeolite catalyst which does not contain significant amounts of non-zeolitic binder and contains first crystals of a first zeolite, a binder comprising second crystals of a second zeolite, and said hydrogenation/dehydrogenation metal, said process comprising:
   (i) providing said first crystals of said first zeolite;
   (ii) forming a silica bound aggregate comprising at least a portion of said at least one hydrogenation/dehydrogenation metal and said first crystals of said first zeolite; and,
   (iii) converting to said second zeolite the silica binder of said silica bound aggregate,
wherein said portion of said at least one hydrogenation/dehydrogenation metal is added during the preparation of said zeolite bound zeolite catalyst after step (i).

21. The process recited in claim 20, wherein said at least one hydrogenation/dehydrogenation metal is a Group VIIIA metal.

22. The process recited in claim 21, wherein said crystals are intergrown and form at least a partial coating on said first crystals.

23. The process recited in claim 22, wherein said first crystals of said first zeolite have an average particle size greater than about 0.1 micron and said second crystals of said second zeolite have an average particle size that is less than said first crystals of said first zeolite.

24. The process recited in claim 23, wherein said first zeolite is a structure type selected from the group consisting, of OFF, BEA, MAZ, MEI, FAU EMT, LTL, VFI, MOR, MFI, MFS, MEL, MTW, MTT, FER, EUO, HEU, TON, CHA, ERI, KFI, LEV, and LTA.

25. The process recited in claim 24, wherein said second zeolite is a structure type selected from the group consisting of OFF, BEA, MAZ, MEI, FAU, EMT, LTL, VFI, MOR, MFI, MFS, MEL, MTW, MTT, FER, EUO, HEU, TON, CHA, ERI, KFI, LEV, and LTA.

26. The catalyst recited in claim 25, wherein said first zeolite and said second zeolite are an aluminosilicate zeolite or a gallium silicate zeolite.

27. The process recited in claim 26, wherein said silica bound aggregate is prepared by forming an extrudable mass containing said silica and said first crystals of said zeolite, extruding said extrudable mass to form an extrudate, and calcining the extrudate.

28. The process recited in claim 27, wherein said silica bound aggregate is prepared by forming an extrudate mass which contains said metal, said silica and said first crystals of said first zeolite and extrudating said mass.

29. The process recited in claim 28, wherein said catalyst is prepared by aging at elevated temperatures a silica-bound aggregate containing said hydrogenation/dehydrogenation metal and first crystals of said first zeolite in an aqueous ionic solution containing a source of hydroxy ions sufficient to convert the silica binder to the second zeolite.

30. The process recited in claim 29, wherein said hydrogenation/dehydrogenation metal is added to said aqueous solution.

31. The process recited in claim 30, wherein said first zeolite and said second zeolite have LTL structure type.

32. The process recited in claim 31, wherein said first zeolite and said second zeolite have a MFI or MEL structure type.

33. The process recited in claim 32, wherein said zeolite bound zeolite catalyst contains less than 5% by weight of non-zeolitic binder based on weight of said first zeolite and said second zeolite.

34. The process recited in claim 33, wherein said at least hydrogenation/dehydrogenation metal comprises a noble metal.

35. The process recited in claim 34, wherein said first zeolite has a silica to alumina mole ratio from 70 to 700 or a silica to gallia mole ratio from 20 to 500.

36. The process recited in claim 35, wherein said second zeolite has a silica to alumina mole ratio greater than 200 or a silica to gallia mole ratio greater than 100.

37. The process recited in claim 28, wherein hydrogenation/dehydrogenation metal is incorporated into said extrudate prior to calcining.

38. The process recite in claim 37 wherein said hydrogenation metal/dehydrogenation metal is incorporated into said extrudable mass by physical mixing.

39. The process recited in claim 38, wherein said second zeolite has lower acidity than said first zeolite.

40. The process recited in claim 28, wherein said hydrogenation/dehydrogenation metal is present in said catalyst in an amount of from about 0.05 to about 3.0 wt. percent.

41. The process recited in claim 40, wherein said hydrogenation/dehydrogenation metal is incorporated into extrudate after said calcining of said extrudate.

* * * * *